(12) United States Patent
Riedijk

(10) Patent No.: US 9,152,841 B1
(45) Date of Patent: Oct. 6, 2015

(54) CAPACITIVE FINGERPRINT SENSOR WITH IMPROVED SENSING ELEMENT

(71) Applicant: FINGERPRINT CARDS AB, Göteborg (SE)

(72) Inventor: Frank Robert Riedijk, Delft (NL)

(73) Assignee: FINGERPRINT CARDS AB, Gothenburg (SE)

( * ) Notice: Subject to any disclaimer, the term of this patent is extended or adjusted under 35 U.S.C. 154(b) by 0 days.

(21) Appl. No.: 14/548,834

(22) Filed: Nov. 20, 2014

(51) Int. Cl.
  *G06K 9/00* (2006.01)
  *G07C 9/00* (2006.01)
  *G06K 9/03* (2006.01)

(52) U.S. Cl.
  CPC ............ *G06K 9/0002* (2013.01); *G06K 9/0008* (2013.01); *G06K 9/036* (2013.01); *G07C 9/00158* (2013.01)

(58) Field of Classification Search
  None
  See application file for complete search history.

(56) References Cited

U.S. PATENT DOCUMENTS

| | | | | |
|---|---|---|---|---|
| 6,320,394 | B1 * | 11/2001 | Tartagni ...................... | 324/671 |
| 6,927,581 | B2 * | 8/2005 | Gozzini ....................... | 324/663 |
| 6,987,871 | B2 * | 1/2006 | Kalnitsky et al. ............ | 382/124 |
| 7,864,992 | B2 | 1/2011 | Riedijk et al. | |
| 2005/0031175 | A1 * | 2/2005 | Hara et al. ................... | 382/124 |
| 2013/0271422 | A1 | 10/2013 | Hotelling et al. | |
| 2013/0294662 | A1 | 11/2013 | Franza et al. | |
| 2013/0314105 | A1 | 11/2013 | Setlak et al. | |

OTHER PUBLICATIONS

Shimamura, et al. "Capacitive-Sensing Circuit Technique for Image Quality Improvement on Fingerprint Sensor LSIs", IEEE, pp. 1080-1087, May 2010.*
Lee, K. et al., "A 500dpi Capacitive-Type CMOS Fingerpint Sensor With Pixel-Level Adaptive Image Enhancement Scheme," ISSCC 2002 / Session 21 / TD: Sensors and Microsystems / 21.3, 2002 IEEE International Solid-State Circuits Conference, 10 pages.

* cited by examiner

*Primary Examiner* — Daniel Mariam
(74) *Attorney, Agent, or Firm* — Remarck Law Group PLC

(57) ABSTRACT

The present invention relates to a capacitive fingerprint sensing device comprising a semiconductor substrate; and an array of sensing elements formed on the semiconductor substrate. Each of the sensing elements comprises a protective dielectric top layer; a sensing structure arranged underneath the top layer; and a charge amplifier connected to the sensing structure. The charge amplifier comprises a negative input connected to the sensing structure; a positive input; an output providing a sensing signal; a feedback capacitor; and a sense transistor having a gate constituting the negative input. The sense transistor is formed in an insulated well in the semiconductor substrate. The fingerprint sensing device further comprises excitation signal providing circuitry connected to the positive input of the charge amplifier and the well for changing electric potentials of the sensing structure and the well, to thereby reduce the influence of parasitic capacitances in the sensing element.

15 Claims, 7 Drawing Sheets

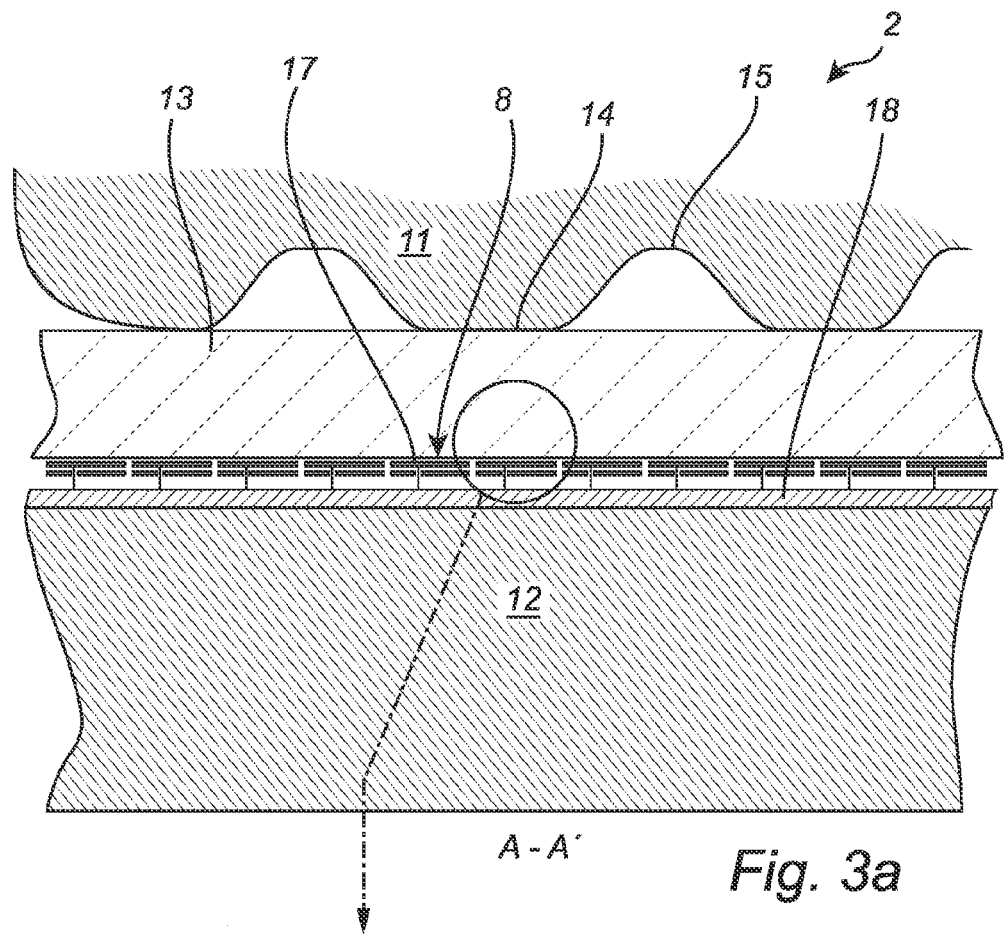
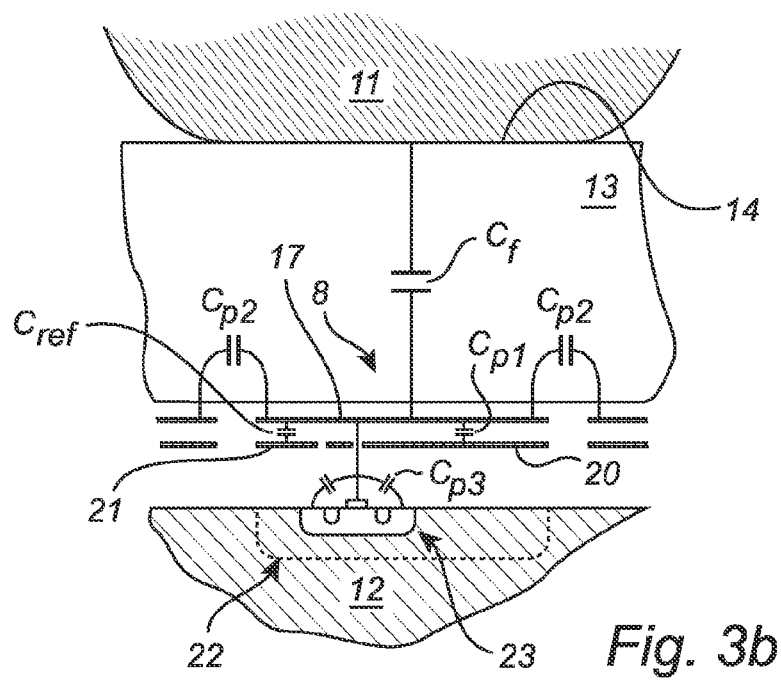

CAPACITIVE FINGERPRINT SENSOR WITH IMPROVED SENSING ELEMENT

FIELD OF THE INVENTION

The present invention relates to a capacitive fingerprint sensing device and to a method of sensing a fingerprint pattern.

BACKGROUND OF THE INVENTION

Various types of biometric systems are used more and more in order to provide for increased security and/or enhanced user convenience.

In particular, fingerprint sensing systems have been adopted in, for example, consumer electronic devices, thanks to their small form factor, high performance and user acceptance.

Among the various available fingerprint sensing principles (such as capacitive, optical, thermal etc), capacitive sensing is most commonly used, in particular in applications where size and power consumption are important issues.

All capacitive fingerprint sensors provide a measure indicative of the capacitance between each of several sensing structures and a finger placed on or moved across the surface of the fingerprint sensor.

Some capacitive fingerprint sensors passively read out the capacitance between the sensing structures and the finger. This, however, requires a relatively large capacitance. Therefore such passive capacitive sensors are typically provided with a very thin protective layer covering the sensing structures, which makes such sensors rather sensitive to scratching and/or ESD (electro-static discharge).

U.S. Pat. No. 7,864,992 discloses an active capacitive fingerprint sensing device in which a driving signal is injected into the finger by pulsing a conductive drive structure arranged in the vicinity of the sensor array and measuring the resulting change of the charge carried by the sensing structures in the sensor array.

Although the fingerprint sensing system according to U.S. Pat. No. 7,864,992 provides for an excellent combination of fingerprint image quality and sensor protection, it would, in some applications be desirable to be able to acquire a high-quality fingerprint image without the use of a separate conductive drive structure. In particular, there appears to be room for improvement for "difficult" fingers, such as dry fingers.

An alternative active fingerprint sensing device is described in the paper "*A 500 dpi Capacitive-Type CMOS Fingerprint Sensor with Pixel-Level Adaptive Image Enhancement Scheme*" by Kwang-Hyun Lee and Euisik Yoon (ISSCC 2002/session 21/TD: Sensors and microsystems/21.3). In this fingerprint sensing device, an excitation pulse is applied to the sensing electrode of each pixel instead of to the finger. The potential of the finger is assumed to be substantially constant.

This fingerprint sensor would appear to be usable without a separate conductive drive structure. However, the fingerprint sensor described in "A 500 dpi Capacitive-Type CMOS Fingerprint Sensor with Pixel-Level Adaptive Image Enhancement Scheme" is said to be configured to exhibit a capacitance to the finger (the capacitance that is measured) in the range of 0 fF to 200 fF. In the field of fingerprint sensing, this is a relatively large capacitance, which indicates that the protective coating provided on top of the sensing electrodes is very thin. Actually, the protective coating is referred to as a "passivation layer", which is generally understood to be a layer of SiO or SiN that has a thickness of around 1 μm. A fingerprint sensor with such a thin protective coating would not be robust enough for many important applications, including mobile device applications.

It would thus be desirable to provide a more robust capacitive fingerprint sensing device in which the excitation pulse is applied to the sensing electrode, which is at the same time capable of achieving a high quality fingerprint representation.

SUMMARY

In view of above-mentioned and other drawbacks of the prior art, it is an object of the present invention to provide an improved capacitive fingerprint sensing device.

According to a first aspect of the present invention, it is therefore provided a capacitive fingerprint sensing device for sensing a fingerprint pattern of a finger, the fingerprint sensing device comprising a semiconductor substrate; and an array of sensing elements formed on the semiconductor substrate, wherein each of the sensing elements comprises: a protective dielectric top layer to be touched by the finger; an electrically conductive sensing structure arranged underneath the top layer; and a charge amplifier connected to the sensing structure for providing a sensing signal indicative of a change of a charge carried by the sensing structure resulting from a change in a potential difference between the finger and the sensing structure, the charge amplifier comprising: a negative input connected to the sensing structure; a positive input; an output providing the sensing signal; a feedback capacitor connected between the negative input and the output; and a sense transistor having a gate constituting the negative input, wherein the sense transistor is formed in a well in the semiconductor substrate, an interface between the well and the substrate being configured in such a way that current can be prevented from flowing between the well and the substrate; and wherein the charge amplifier is configured in such a way that a potential at the negative input substantially follows a potential at the positive input, wherein the fingerprint sensing device further comprises: excitation signal providing circuitry, the excitation signal providing circuitry being: connected to the positive input and configured to change a potential at the positive input from a first potential to a second potential, to thereby change a potential of the sensing structure, thereby providing the change in potential difference between the finger and the sensing structure; and connected to the well for changing a potential of the well from a third potential to a fourth potential, a difference between the third potential and the fourth potential being substantially equal to a difference between the first potential and the second potential, to thereby reduce an influence of a parasitic capacitance between the sensing structure and the well, and between the sense transistor and the well.

The semiconductor substrate may advantageously be a doped semiconductor substrate, and the well may be a portion of the substrate doped to opposite polarity with respect to the semiconductor substrate (if the semiconductor substrate is p-doped, the well may be n-doped, and if the semiconductor substrate is n-doped, the well may be p-doped. This is one way of achieving an interface between the well and the substrate that is configured in such a way that a current can be prevented from flowing between the well and the substrate. In particular, the well and the substrate may be kept at such electrical potentials that no current flows through the diode formed at the interface between the substrate and the well.

Alternatively, an insulating layer may be provided between the substrate and the well, for instance in the form of a thin layer of glass. Such an insulating layer will also prevent current from flowing between the well and the substrate.

The charge amplifier converts charge at the negative input to a voltage at the output. The gain of the charge amplifier is determined by the capacitance of the feedback capacitor.

That the charge amplifier is configured in such a way that the potential at the negative input substantially follows the potential at the positive input should be understood to mean that a change in the potential at the positive input results in a substantially corresponding change in the potential at the negative input. Depending on the actual configuration of the charge amplifier, the potential at the negative input may be substantially the same as the potential at the positive input, or there may be a substantially constant potential difference between the positive input and the negative input. If, for instance, the charge amplifier is configured as a single stage amplifier, the potential difference will be the gate-source voltage of the sense transistor.

It should be noted that the output of the charge amplifier need not be directly connected to the feedback capacitor, and that there may be additional circuitry between the output and the feedback capacitor. This circuitry could also be placed outside the matrix of sensing elements.

The excitation signal providing circuitry could be switching circuitry configured to switch between two or more different potentials provided on different lines. Alternatively or in combination, the excitation signal providing circuitry may comprise at least one signal source configured to provide a time-varying potential, such as a square wave voltage signal or a sine wave voltage signal.

The sensing structure may advantageously be provided in the form of a metal plate, so that a kind of parallel plate capacitor is formed by the sensing structure (the sensing plate), the local finger surface, and the protective coating (and any air that may locally exist between the local finger surface and the protective coating).

The protective coating may advantageously be at least 20 μm thick and have a high dielectric strength to protect the underlying structures of the fingerprint sensing device from wear and tear as well as ESD. Even more advantageously, the protective coating may be at least 50 μm thick. In embodiments, the protective coating may be a few hundred μm thick.

The present invention is based upon the realization that the application of the excitation signal to the sensing electrode (and to the sense transistor) will require attention to a substantial parasitic capacitance that may not be visible if the excitation signal is instead applied to the finger, and that the influence of such parasitic capacitance needs to be considerably reduced in order to be able to sense very small capacitances—in the order of 0.1 fF—between the sensing structure and the finger. Sensing such small capacitances may in turn be required to enable the use of the thick protective coating providing for improved robustness.

If the excitation signal is applied to the finger, and the sensing structure is kept at a fixed potential, say ground, then the measurement of the capacitance between sensing structure and finger will not be disturbed by any parasitic capacitance between the sensing structure and the charge amplifier, and/or between the sensing structure and the semiconductor substrate in which the charge amplifier is formed, since the potential of the sensing structure and the relevant parts of the charge amplifier (and the semiconductor substrate) will be the same (or there will be a constant potential difference between the sensing structure and the input stage of the charge amplifier and the semiconductor substrate). If, however, the excitation signal is applied to the sensing structure, there will be a time varying potential difference between the sensing structure and the semiconductor substrate. Simulations show that the parasitic capacitance between the sensing structure and the semiconductor structures (typically n-well, p-well and/or semiconductor substrate) adjacent to the connection between the sensing structure and the input stage of the charge amplifier may be in the order of 10 fF, while the capacitance to be sensed (between the sensing structure and the finger) may be as low as 0.1 fF or less. Furthermore, the above-mentioned parasitic capacitance may typically be unknown and be different for different sensing elements due to variations in the semiconductor manufacturing process.

The present inventor has now realized that the influence of this parasitic capacitance between sensing structure and semiconductor structures in the fingerprint sensing device can be considerably reduced by providing excitation signal providing circuitry configured to change a potential of the well in which the sense transistor of the charge amplifier is formed. Hereby, the potential of the well, which is the semiconductor structure adjacent to the connection between the sensing structure and the sense transistor (input stage of the charge amplifier) can be controlled to follow the potential of the sensing structure so that the potential difference between the well and the sensing structure is kept substantially constant, at least at points in time that are relevant to the measurement of the capacitance between the sensing structure and the finger.

Which points in time are relevant to the measurement may be different depending on the measurement method used, and the skilled person will be able to determine such points in time, for example based on circuit simulation, without undue burden. For example, in the case of so-called correlated double-sampling where the sensing signal is sampled at two sampling times, those sampling times may be the points in time that are relevant to the measurement.

When providing an excitation signal to the finger through a direct conductive electrical connection, or in other words galvanically driving the finger, the potential difference between the finger surface touching the sensor array and the sensing structures in the sensor array may be different for fingers with different electrical properties. For instance, the potential difference may be lower for dry fingers, resulting in a "weaker" fingerprint image which may be difficult to analyze.

Various embodiments of the present invention provide for a robust capacitive fingerprint sensor capable of acquiring a high quality fingerprint representation without the need for a conductive drive electrode in galvanic connection with the finger. This provides for an improved fingerprint acquisition from "difficult" fingers (in particular dry fingers). The representation of the fingerprint pattern may, for example, be raw fingerprint image data, or the data may have been processed and may then be provided in the form of conditioned image data, as fingerprint template data or in any other form.

Additionally, since successful operation of the fingerprint sensing device according to embodiments of the present invention does not rely upon a varying potential of the finger, the finger can be allowed to be grounded (or at least heavily loaded) by a conductive part of the product in which the fingerprint sensing device is included.

Furthermore, the absence of a conductive structure (such as a conducting frame surrounding the sensor array) simplifies integration of the fingerprint sensor into various devices, such as mobile phones and computers. Moreover, the design of the fingerprint sensor system can be made less obtrusive and the finish of the product including the fingerprint sensor system can be improved.

According to various embodiments of the present invention, the excitation signal providing circuitry may further be configured to simultaneously keep the positive input of the charge amplifier at the first potential and the well at the third potential; and simultaneously keep the positive input of the charge amplifier at the second potential and the well at the fourth potential. Hereby, the well may be subjected to a voltage swing that is substantially of the same magnitude as the voltage swing of the sensing structure. This will allow the influence of the parasitic capacitance between the sensing structure and the well to be removed or at least considerably reduced.

Various embodiments of the fingerprint sensing device according to the present invention may further comprise sampling circuitry connected to the output of the charge amplifier, and configured to sample the sensing signal at a first sampling time when the positive input of the charge amplifier is kept at the first potential and the well is kept at the third potential and at a second sampling time when the positive input of the charge amplifier is kept at the second potential and the well is kept at the fourth potential.

The procedure of sampling the sensing signal at first and second sampling times is generally referred to as correlated double sampling and removes much of the offset as well as at least low-frequency components of the common mode noise that the fingerprint sensing device may be subjected to. By ensuring that the potentials of the sensing structure and the well, respectively, are at least synchronized with the sampling times, the influence of the parasitic capacitance between the sensing structure and the well can be removed or at least considerably reduced.

In various embodiments, furthermore, the third potential may advantageously be substantially equal to the first potential, and the fourth potential may be substantially equal to the second potential.

Moreover, the excitation signal providing circuitry may have an output connected to each of the positive input and the well for simultaneously changing the potential at the positive input and the potential of the well from the first potential to the second potential.

According to various embodiments, moreover, the fingerprint sensing device may further comprise a shielding structure arranged between the sensing structure and the substrate. The excitation signal providing circuitry may further be connected to the shielding plate and configured to change a potential of the shielding plate from a fifth potential to a sixth potential, a difference between the fifth potential and the sixth potential being substantially equal to a difference between the first potential and the second potential.

Hereby, the sensing structure may effectively be shielded from other possibly underlying parts of the sensing element, such as connecting lines in metal layers and/or connecting lines and/or semiconductor circuitry formed in the semiconductor substrate. This will further reduce the influence of parasitic capacitances in the sensing element.

The fifth potential may advantageously be equal to the above-mentioned third (and/or first) potential, and the sixth potential may advantageously be equal to the above-mentioned fourth (and/or second) potential. For example, the shielding plate may advantageously be directly conductively connected to the well.

According to a first set of embodiments, the sense transistor may be an NMOS-transistor or a PMOS-transistor, and the well may be a p-well or an n-well, respectively.

According to a second set of embodiments, a p-well and/or an n-well may be formed in the well being connected to the excitation signal providing circuitry. When at least one p-well and at least one n-well are formed in the well, the well may sometimes be referred to as an iso-well.

Furthermore, the well may be common to a plurality of sensing elements. For instance, the well may be an iso-well surrounding n-wells and p-wells of several sensing elements. The excitation signal providing circuitry may be connected to the iso-well and to the well(s) formed inside the iso-well, and configured to change the voltages of the iso-well and the well(s) formed inside the iso-well.

According to various embodiments, each of the sensing elements may further comprise a reset switch comprising at least one reset transistor connected between the negative input and the output of the charge amplifier and controllable to discharge the feedback capacitor, wherein the reset transistor is formed in the well.

The gate of the reset transistor may be connected to a fixed potential selected in relation to the above-mentioned third and fourth potentials to keep the reset transistor conducting when it is controlled to discharge the feedback capacitor, and to a varying potential, which may be provided by the excitation signal providing circuitry, to keep the reset transistor non-conducting to allow charging of the feedback capacitor.

According to various embodiments, furthermore, each of the sensing elements may additionally comprise drive signal providing circuitry comprising at least one drive transistor connected to the sensing structure and controllable to provide a driving signal directly to the sensing structure, wherein the drive transistor is formed in the well.

For example, the drive transistor may be controllable to connect the sensing structure to the excitation signal providing circuitry when the sensing element is in its 'drive' state and to disconnect the sensing structure from the excitation signal providing circuitry when the sensing element is in its 'sense' state. To that end, the gate of the drive transistor may be connected to a fixed potential selected in relation to the above-mentioned third and fourth potentials to keep the drive transistor conducting in the 'drive' state and to a varying potential, which may be provided by the excitation signal providing circuitry, to keep the drive transistor non-conducting in the 'sense' state.

Through the provision of the drive signal providing circuitry, the sensing structures of sensing elements (pixels) adjacent the sensing element (pixel) that is currently sensing can be made to "follow" the potential of the sensing structure of the sensing element that is currently sensing without having to operate the charge amplifier of that sensing element. This provides for reduced power consumption of the fingerprint sensing device. Each sensing element may advantageously be programmable between at least a 'sense' state and a 'drive' state. There may also be a third state in which the sensing structure may be connected to a fixed potential or be electrically floating. Hereby, the influence of parasitic capacitances between the sensing structure and sensing structures of adjacent sensing elements can be removed or at least considerably reduced.

The fingerprint sensing device according to various embodiments of the present invention may further advantageously comprise readout circuitry connected to each of the sensing elements and configured to provide a representation of the fingerprint pattern based on the sensing signal from each of the sensing elements.

This fingerprint sensing device may advantageously be comprised in an electronic device further comprising processing circuitry configured to: acquire the representation of the fingerprint pattern from the fingerprint sensing device; authenticate a user based on the representation; and perform at least one user-requested process only if the user is authenticated based on the representation. The electronic device may, for example, be a handheld communication device, such as a mobile phone or a tablet, a computer, or an electronic wearable item such as a watch or similar.

According to a second aspect of the present invention, there is provided a method of sensing a fingerprint pattern of a finger using a fingerprint sensing device comprising a doped semiconductor substrate; and an array of sensing elements formed on the semiconductor substrate, wherein each of the sensing elements includes an electrically conductive sensing structure connected to the gate of a sense transistor formed in a well in the semiconductor substrate, the well being doped to opposite polarity with respect to the semiconductor substrate, the method comprising the steps of, for each of the sensing elements: changing a potential of the sensing structure from a first potential to a second potential; changing a potential of the well from a third potential to a fourth potential, a difference between the third potential and the fourth potential being substantially equal to a difference between the first potential and the second potential; and providing a sensing signal indicative of a change of a charge carried by the sensing structure resulting from a change in a potential difference between the finger and the sensing structure achieved by the change in potential of the sensing structure from the first potential to the second potential.

In an embodiment of the method according to the present invention, the potential of the well may be changed in such a way that: the well is at the third potential at the same time as the sensing structure is at the first potential; and the well is at the fourth potential at the same time as the sensing structure is at the second potential.

According to various embodiments of the present invention, the method may further comprise the step of changing a potential of each sensing structure in a plurality of adjacent sensing elements from a seventh potential to an eighth potential, a difference between the seventh potential and the eighth potential being substantially equal to a difference between the first potential and the second potential.

Hereby, the influence of parasitic capacitances between the sensing structure and sensing structures of adjacent sensing elements can be removed or at least considerably reduced.

Further embodiments of, and effects obtained through this second aspect of the present invention are largely analogous to those described above for the first aspect of the invention.

In summary, the present invention relates to a capacitive fingerprint sensing device comprising a semiconductor substrate; and an array of sensing elements formed on the semiconductor substrate. Each of the sensing elements comprises a protective dielectric top layer; a sensing structure arranged underneath the top layer; and a charge amplifier connected to the sensing structure. The charge amplifier comprises a negative input connected to the sensing structure; a positive input; an output providing a sensing signal; a feedback capacitor; and a sense transistor having a gate constituting the negative input. The sense transistor is formed in an insulated well in the semiconductor substrate. The fingerprint sensing device further comprises excitation signal providing circuitry connected to the positive input of the charge amplifier and the well for changing electric potentials of the sensing structure and the well, to thereby reduce the influence of parasitic capacitances in the sensing element.

BRIEF DESCRIPTION OF THE DRAWINGS

These and other aspects of the present invention will now be described in more detail, with reference to the appended drawings showing an example embodiment of the invention, wherein:

FIG. 3a is a schematic cross-section view of a portion of the fingerprint sensing device in FIG. 2;

FIG. 3b is an enlargement of a part of the cross-section view in FIG. 3a illustrating various capacitances in the fingerprint sensing device;

DETAILED DESCRIPTION OF EXAMPLE EMBODIMENTS

In the present detailed description, various embodiments of the fingerprint sensing device and method according to the present invention are mainly described with reference to a fingerprint sensing device in which positive input of the charge amplifier and the well in which the sense transistor comprised in the charge amplifier is formed are connected together and accordingly controlled by the excitation signal providing circuitry to follow the same time-varying electrical potential (in relation to a reference potential, such as electrical ground). The shielding plate between the sensing structure (plate) and the underlying structures in the fingerprint sensing device is also connected to the positive input of the charge amplifier. Furthermore, the feedback capacitor is formed by the sensing plate, a reference plate in the same metal layer as the above-mentioned shielding plate and the dielectric layer between the sensing plate and the reference plate. Moreover, the fingerprint sensing device is illustrated as a touch sensor dimensioned and configured to acquire a fingerprint representation from a stationary finger.

It should be noted that this by no means limits the scope of the present invention, which equally well includes, for example, a fingerprint sensing device in which the electrical potentials of the positive input of the charge amplifier, the above-mentioned well and/or the shielding plate are varied between different potentials, as long as the potential step for each is substantially the same. Furthermore, the feedback capacitor may be formed using other structures in the sensing element. For instance, the sensing element may be configured such that the gate and drain of the sense transistor may be used as feedback capacitor. Other sensor array configurations, such as a so-called swipe sensor (or line sensor) for acquiring a fingerprint representation from a moving finger, are also within the scope of the present invention as defined by the appended claims.

Figure 1:
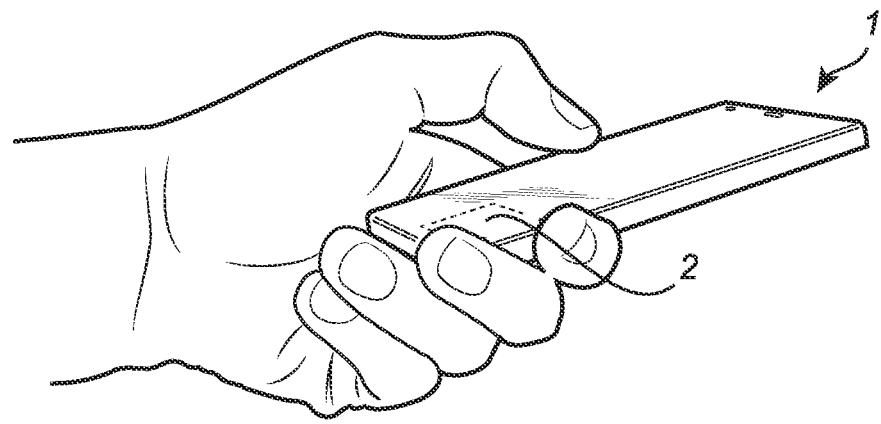
FIG. 1 schematically illustrates an application for a fingerprint sensing device according to an example embodiment of the present invention.

FIG. 1 schematically illustrates an application for a fingerprint sensing device according to an example embodiment of the present invention, in the form of a mobile phone 1 with an integrated fingerprint sensing device 2. The fingerprint sensing device 2 may, for example, be used for unlocking the mobile phone 1 and/or for authorizing transactions carried out using the mobile phone, etc.

Figure 2:
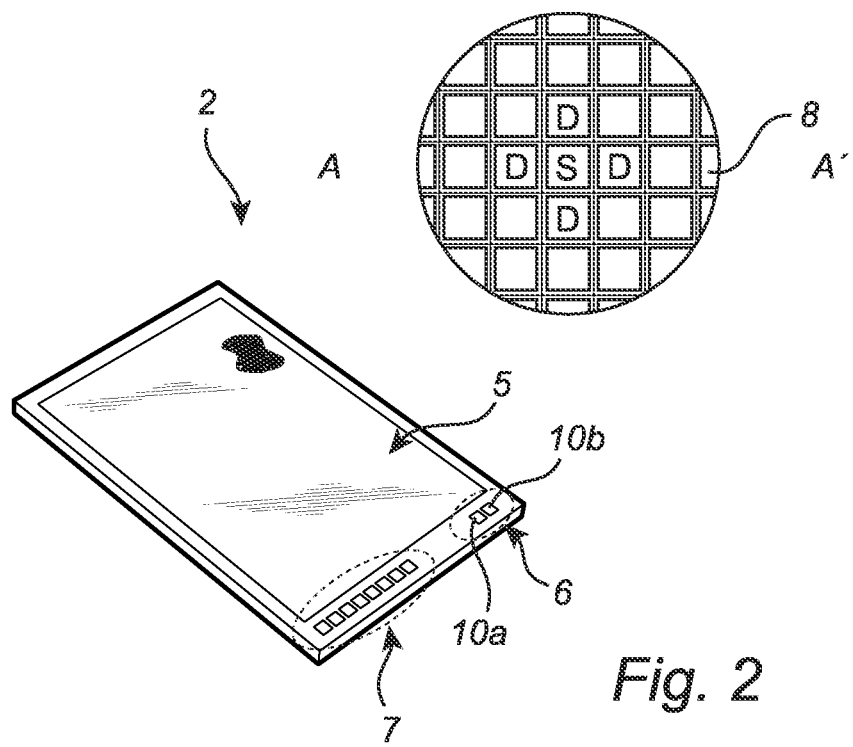
FIG. 2 schematically shows the fingerprint sensing device in FIG. 1.

FIG. 2 schematically shows the fingerprint sensing device 2 comprised in the mobile phone 1 in FIG. 1. As can be seen in FIG. 2, the fingerprint sensing device 2 comprises a sensor array 5, a power supply interface 6 and a communication interface 7. The sensor array 5 comprises a large number of sensing elements 8 (only one of the sensing elements has been indicated with a reference numeral to avoid cluttering the drawing), each being controllable to sense a distance between a sensing structure (top plate) comprised in the sensing element 8 and the surface of a finger contacting the top surface of the sensor array 5. In the enlarged portion of the sensor array 5 in FIG. 2, a first sensing element is marked 'S' for sense and a second group of neighboring sensing elements are marked 'D' for drive.

The power supply interface 6 comprises first 10a and second 10b contact pads, here shown as bond pads, for connection of a supply voltage Vsupply to the fingerprint sensor 2.

The communication interface 7 comprises a number of bond pads for allowing control of the fingerprint sensor 2 and for acquisition of fingerprint data from the fingerprint sensor 2.

FIG. 3a is a schematic cross section of a portion of the fingerprint sensing device 2 in FIG. 2 taken along the line A-A' as indicated in FIG. 2 with a finger 11 placed on top of the sensor array 5. Referring to FIG. 3a, the fingerprint sensing device 2 comprises a doped semiconductor substrate 12, the plurality of sensing elements 8 formed on the semiconductor substrate 12, and a protective coating 13 on top of the sensing elements. The surface of the finger 11 comprises ridges 14 that are in contact with the protective coating 13 and valleys 15 that are spaced apart from the protective coating 13.

As is schematically indicated in FIG. 3a, each sensing element 8 comprises a sensing structure in the form of a sensing plate 17 adjacent to the protective coating 13. Below the sensing plate 17 are additional metal structures and active semiconductor circuitry schematically indicated by the hatched region 18 in FIG. 3a.

FIG. 3a is approximately drawn to scale to illustrate the relative dimensions of the protective coating 13, the sensing elements 8 and the ridges 14 and valleys 15 of the finger 11. As can be seen, the protective coating 13 is rather thick, in order to protect the sensing elements from wear and tear and ESD. Needless to say, the protective coating 13 is important for the robustness of the fingerprint sensing device 2. From the relative dimensions in FIG. 3a also follows that the capacitance between sensing structure 17 and finger 11 is very small, especially compared to parasitic capacitances between the sensing plate 17 and other conducting structures adjacent to the sensing plate 17. Examples of such conducting structures include neighboring sensing plates, the abovementioned additional metal structures, the active semiconductor circuitry 18 and the substrate 12.

As is schematically indicated in FIG. 3b, the sensing element 8 comprises, in addition to the sensing plate 17, a shielding plate 20, a reference plate 21, and a charge amplifier 22. The charge amplifier 22 is, in FIG. 3b, only very schematically indicated by the dotted line. The only part of the charge amplifier 22 that is shown in some detail is the sense transistor (MOSFET) 23 to which the sensing plate 17 is connected.

The reason for this type of illustration is to allow indication of the most important parasitic capacitances affecting the sensing element 8.

Indicated in FIG. 3b is the finger capacitance Cf between the sensing plate 17 and the finger 11, the reference capacitance Cref between the sensing plate 17 and the reference plate 21, a first parasitic capacitance Cp1 between the sensing plate 17 and the shielding plate 20, a second parasitic capacitance Cp2 between the sensing plate and a neighboring sensing plate, and a third parasitic capacitance Cp3 between the sensing plate and the well 25 in which the sense transistor 23 is formed (actually between the well 25 and the line connecting the sensing plate 17 with the gate of the sense transistor 23). Cp3 also includes the internal capacitors in the sense transistor itself.

In order to achieve high quality fingerprint sensing using the robust fingerprint sensing device 2 in FIGS. 3a-b, it is of utmost importance to remove or at least reduce the influence of the parasitic capacitances related to the sensing plate 17. This will be clearly understood based on a comparison of approximate magnitudes of the various capacitances in FIG. 3b. The parasitic capacitance Cp1 is in the order of 100 fF, Cp2 is in the order of 10 fF and Cp3 is in the order of 5-10 fF, while the finger capacitance Cf to be sensed in in the order of 0.1 fF.

An example configuration of the sensing elements 8 for removing or at least considerably reducing the influence of the various parasitic capacitances will now be described with reference to FIG. 4a-b.

Figure 4A:
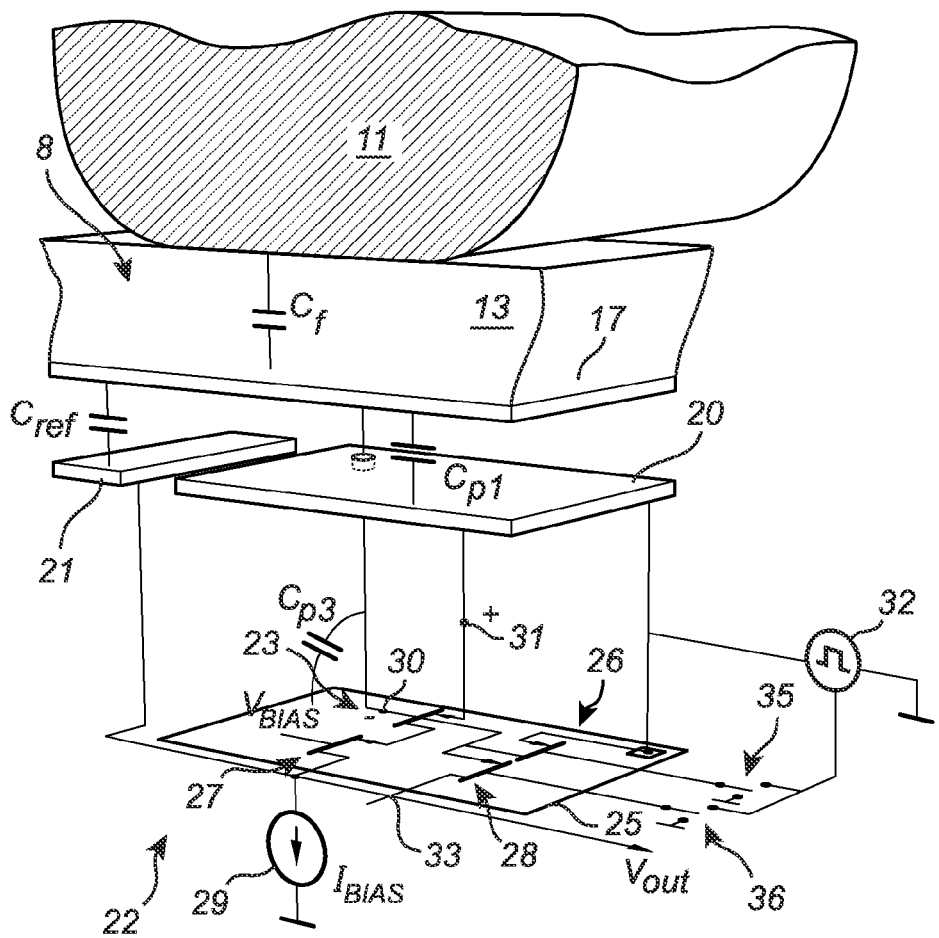
FIG. 4a is a hybrid of a partly structural and partly circuit schematic illustration of a sensing element comprised in the fingerprint sensing device in FIG. 2.

FIG. 4a is a hybrid of a partly structural and partly circuit schematic illustration of the sensing element 8 in FIGS. 3a-b. The protective coating 13, the sensing plate 17, the shielding plate 20 and the reference plate 21 are schematically shown in an exploded perspective view, while the charge amplifier 22 is illustrated in the form of a transistor level circuit schematic.

As is shown in FIG. 4a, this first example of a simple charge amplifier 22 comprises sense transistor 23, cascode transistor 27, reset transistor 28 and bias current source 29. The sense transistor 23, the cascode transistor 27 and the reset transistor 28 are all formed in the same well 25.

Figure 4B:
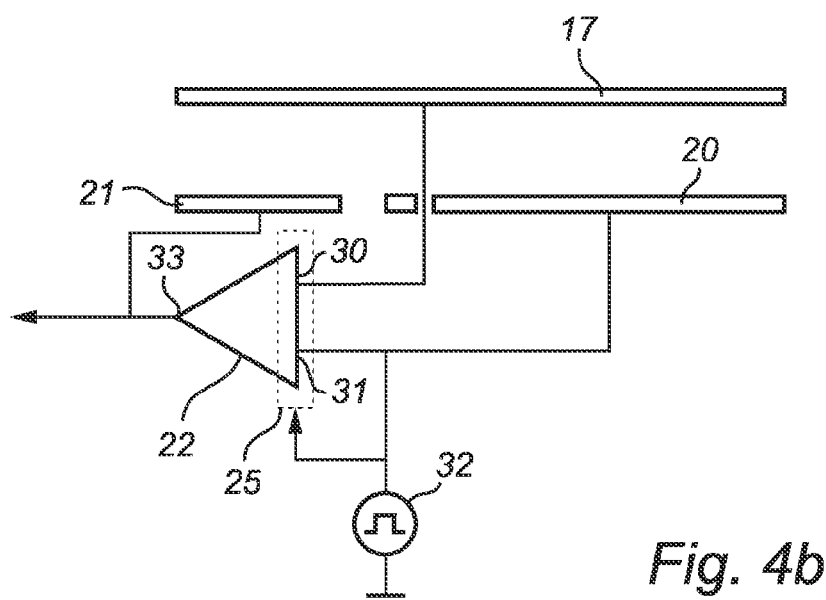
FIG. 4b is a version of FIG. 4a in which the charge amplifier is illustrated using a higher level symbol.

To aid the understanding of the parts and connections in FIG. 4a, the same schematic configuration is also shown in FIG. 4b, on a more abstract level with the transistor circuitry of FIG. 4a replaced by a general symbol for a charge amplifier having its negative input 30 connected to the sensing plate 17, its positive input 31 connected to excitation signal providing circuitry 32, here in the form of a pulse generator, and its output 33 providing a sensing signal Vout indicative of the change in charge carried by the sensing plate 17 resulting from a change in a potential difference between the finger 11 and the sensing plate 17. The change in potential difference between the finger 11 and the sensing plate 17 results from the changing electric potential applied to the sensing plate 17 by the pulse generator 32 via the charge amplifier. A feedback capacitor, formed by the sensing plate 17 and the reference plate 21, is connected between the negative input 30 and the output 33 of the charge amplifier 22. It should be noted that the general functionality of a charge amplifier is well known to one of ordinary skill in the relevant art. FIG. 4b also schematically indicates that the well 25 is connected to the excitation signal providing circuitry 32.

Returning to FIG. 4a, it can be seen that the gate of the sense transistor 23 constitutes the negative input 30 of the charge amplifier 22 and that the source of the sense transistor 23 constitutes the positive input 31 of the charge amplifier 22. The positive input 31 of the charge amplifier 22 is connected to the shielding plate 20, which is in turn connected to the well 25 in which the sense transistor 23 is formed, and to the pulse generator 32.

The sensing element 8 further comprises a drive transistor 26, a drive control switch 35 and a reset control switch 36. The drive control switch 35 is controllable between a first state in which the gate of the drive transistor 26 is connected to the pulse generator 32 and a second state in which the gate of the drive transistor 26 is connected to ground. When the drive control switch 35 is in its first state, the drive transistor 26 will be conducting and thus connect the sensing structure 17 directly to the pulse generator 32. When the drive control switch is in its second state, the drive transistor 26 will be non-conducting. In the latter case, there will thus be no direct connection through the drive transistor 26 between the sensing structure 17 and the pulse generator 32. As can be seen in FIG. 4a, the drive transistor 26 is formed in the well 25. The bias current source 29 can be in the sensing element or outside the sensor array 5.

In the same way, the reset control switch 36 is controllable between a first state in which the reset transistor 28 is non-conducting to allow a potential difference between the sensing plate 17 and the feedback plate 21, and a second state in which the reset transistor 28 is conducting to equalize the potentials of the sensing plate 17 and the feedback plate 21.

Through the configuration of the sensing element 8 in FIG. 4a, the influence of the internal parasitic capacitances Cp1 and Cp3 is removed or at least considerably reduced. Furthermore, driving neighboring sensing structures will remove or at least considerably reduce the influence of the parasitic capacitance Cp2 between neighboring sensing plates 17 indicated in FIG. 3b. This can be achieved by either controlling neighboring sensing elements to be in their 'sense' state or in their 'drive' state, where the 'drive' state has the advantage of providing for a lower current consumption of the fingerprint sensing device 2.

It should be noted that the present invention is not limited to the particular sensing element design of FIG. 4a, but that various elements of the sensing element can be realized in many different ways readily apparent to one of ordinary skill in the art based on the present disclosure. For instance, the charge amplifier may be provided in the form of a two-stage amplifier with differential inputs.

Figure 5:
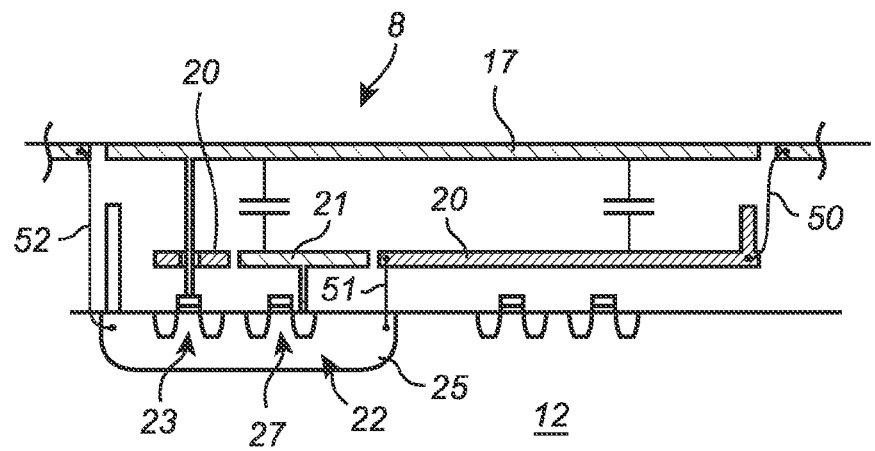
FIG. 5 is a conceptual cross-section illustration of a part of the sensing element in FIG. 4a comprising an n-well.

To further aid in the understanding of various embodiments of the present invention, another cross-section of a first implementation of the sensing element 8 in FIG. 4a is provided in FIG. 5. The illustration in FIG. 5 mainly differs from that in FIG. 4a in that the physical transistor configuration of some of the transistors (the sense transistor 23 and the cascode transistor 27) comprised in the charge amplifier 22 is shown, while the relations in terms of electric potentials of various parts of the sensing element 8 (and neighboring sensing elements) are conceptually indicated using "bootstraps" 50, 51 and 52.

The main purpose of FIG. 5 is to show that the above-mentioned well 25 that is controlled to "follow" the potential of the sensing plate 17 is here an n well that is formed in a p-doped substrate 12. Obviously, the well 25 may alternatively be a p-well that is formed in an n-doped substrate.

Figure 6:
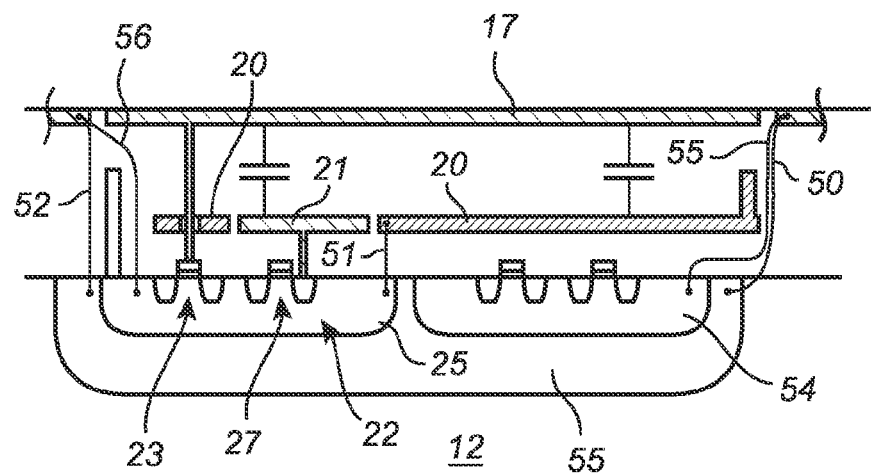
FIG. 6 is a conceptual cross-section illustration of a part of the sensing element in FIG. 4a comprising an iso-well.

FIG. 6 is a similar drawing as FIG. 5 and schematically illustrates a second implementation of the sensing element 8 in FIG. 4a, which differs from what is shown in FIG. 6 in that the n-well 25 and a p-well 54 are both formed in an iso-well 55 that is in turn formed in the substrate 12 (which may be n-doped, p-doped or undoped). In this implementation the iso-well 55, as well as the n-well 25 and the p-well 54, is controlled to follow the potential of the sensing plate 17, as is schematically illustrated by the additional "bootstraps" 53, 54. Specifically there can be potential differences between the wells.

For example, referring to FIG. 6, the iso-well 55 and the n-well 25 may be kept at the same potential, while the potential of the p-well 54 may follow the potential of the iso-well/n-well, but at a different (typically lower) potential Exemplary operation of the fingerprint sensing device 2 according to various embodiments of the present invention will now be described with reference to the functional timing diagrams in FIGS. 7a-c and FIGS. 8a-c.

Figure 7A:
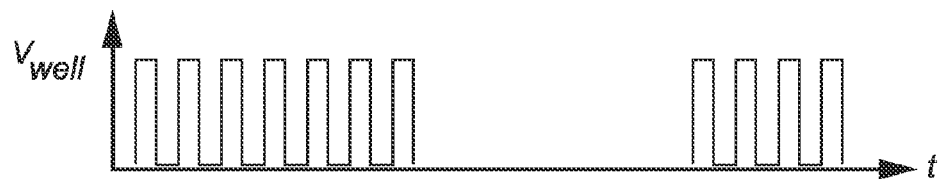
FIGS. 7a-c are timing diagrams schematically illustrating controlling the sensing element in FIG. 4a between its 'drive' state and its 'sense' state.
Figure 7B:
Figure 7C:
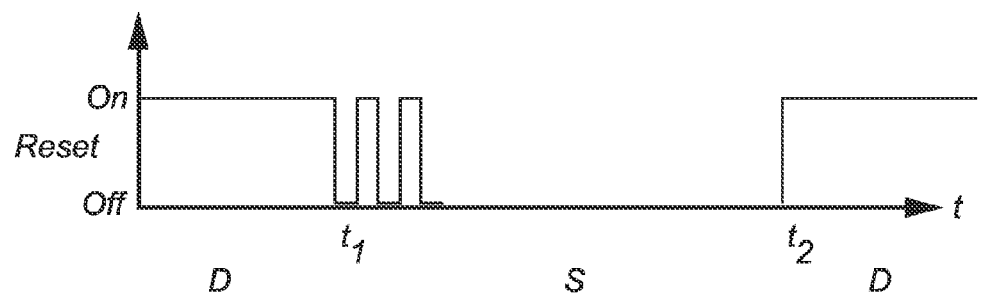

Referring also to FIG. 4a, FIG. 7a schematically shows the behavior potential of the well 25 (and of the sensing plate 17 with an offset), FIG. 7b schematically illustrates a state of the drive control switch 35, and FIG. 7c schematically illustrates a state of the reset control switch 36.

From t0 to t1 in FIGS. 7a-c, the sensing element 8 is in its 'drive' state, at t1, the sensing element 8 is transitioned to its 'sense' state by operating the drive control switch 35, and at t2, the sensing element 8 is transitioned back to its 'drive' state by again operating the drive control switch to connect the sensing plate 17 to the pulse generator 32 through the drive transistor 26.

As is schematically illustrated in FIG. 7a, the well 25 (and the sensing plate 17) exhibits a time varying potential that has substantially the same behavior in the 'sense' state and in the 'drive' state. In the 'drive' state, the time-varying potential is applied to the sensing plate 17 through the drive transistor 26, and in the 'sense' state, the time-varying potential (possibly with an offset depending on the charge amplifier configuration) is applied to the sensing plate 17 via the charge amplifier 22.

As is schematically illustrated in FIG. 7c, the reset control switch 36 is controlled to keep the reset transistor 28 non-conducting when the sensing element 8 is in its 'drive' state and alternating between conducting and non-conducting when the sensing element 8 is in its 'sense' state. An exemplary timing relation between the excitation signal applied to the sensing plate 17 during sensing and the operation of the reset transistor 27 will be described below with reference to FIG. 8a c.

Figure 8A:
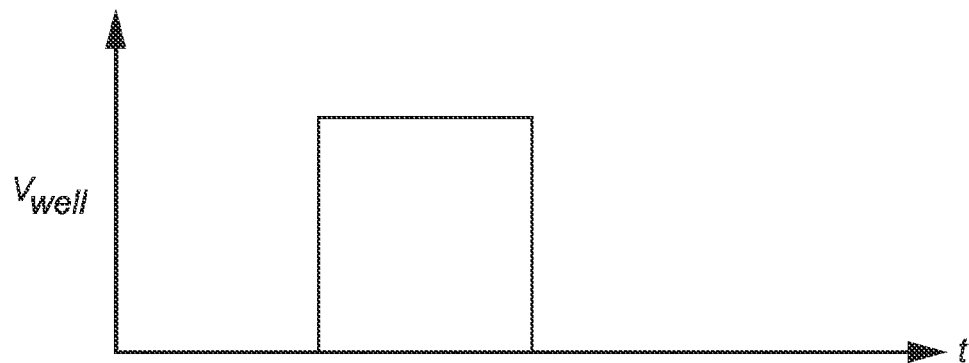
FIGS. 8a-c are graphs schematically illustrating the signal provided to the sensing structure/well and the corresponding sensing signal output from the sensing element.
Figure 8B:
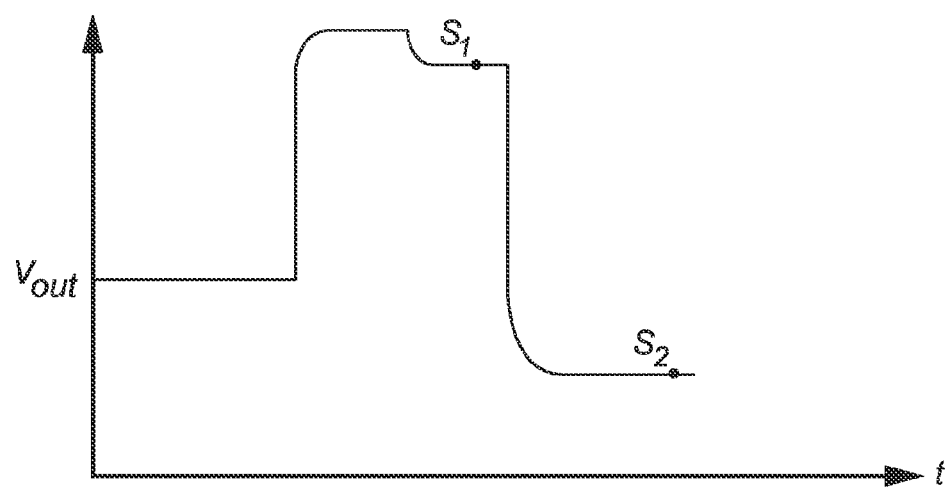
Figure 8C:
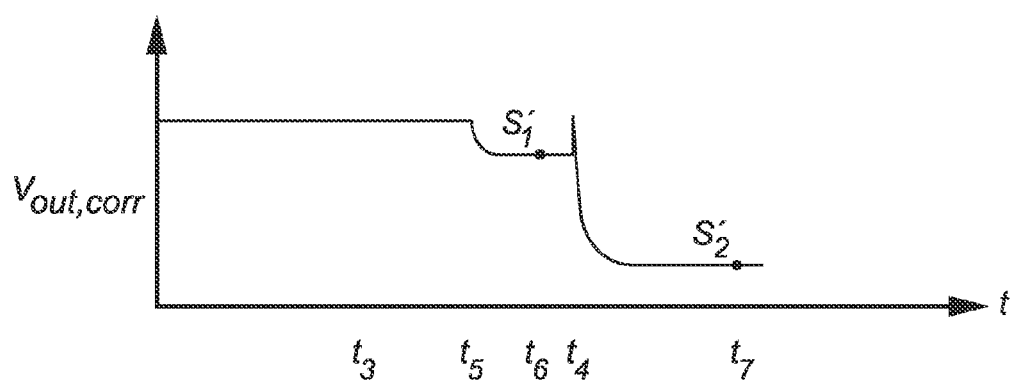

FIG. 8a is an enlarged portion of FIG. 7a, FIG. 8b schematically shows a simulation of the sensing signal, that is, the signal at the output 33 of the charge amplifier 22 in FIG. 4a, and FIG. 8c schematically shows a simulated "corrected" version of the sensing signal that is referenced to a fixed reference potential (such as ground) rather than to the signal applied to the well 25 (which is the local reference potential for the charge amplifier 22 in FIG. 4a).

Referring first to FIG. 8a, the excitation signal applied to the sensing plate 17 goes from low to high potential at t3, and then goes back from high to low at t4. At t3, the reset control switch 36 is operated to make the reset transistor 28 conducting, that is, connect the reference plate 21 to the sensing plate 17 through the reset transistor 28. At t5, the reset control switch 36 is again operated to make the reset transistor 28 non-conducting, that is, bring the charge amplifier in such a state that the output indicates a signal if the charge on the sensing plate 17 changes. At t6, the sensing signal is sampled a first time, resulting in a first sampled value S1. When the excitation signal goes from high to low at t4, there will be a change in the charge on the sensing plate 17 resulting from capacitive coupling with the finger 11, which is assumed to be at a substantially fixed potential (at least on the time scale of the sampling event). This change in charge is translated into a change in the voltage provided by the charge amplifier, that is, a change in the sensing signal Vout. The potential S2 of the sensing signal following the transition from high to low of the excitation signal is sampled at t7. As is evident from FIG. 4a, the sensing signal is related to the potential of the well (FIG. 8a). To get a 'corrected' sensing signal (FIG. 8c), the excitation signal may be subtracted from the sensing signal present at the output 33 of the charge amplifier 22, resulting in corrected sampled voltages S1' and S2'. The difference between S2' and S1' is a measure indicative of the capacitive coupling between the sensing plate 17 and the finger 11.

The corrected signal of FIG. 8c or at least the corrected samples may be obtained in various ways, for instance through the use of an instrumentation amplifier or by using the excitation signal as a reference voltage for the sampling capacitors.

Figure 9:
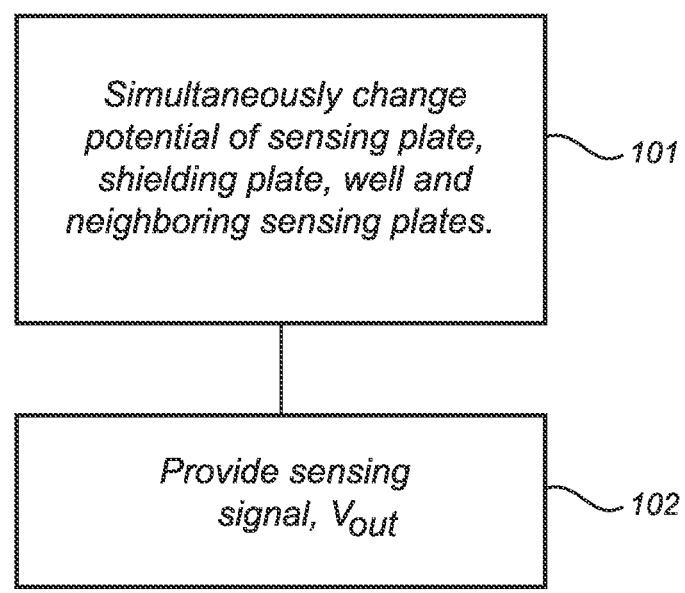
FIG. 9 is a flow-chart schematically illustrating an example embodiment of the method according to the present invention.

An example embodiment of the method according to the present invention will now be described with reference to the flow-cart in FIG. 9. In a first step, 101, the potentials of the sensing plate 17, the shielding plate 20, the well (n-well 25 in FIG. 6 or iso-well 54 in FIG. 7), and neighboring sensing plates are simultaneously changed from a first potential V1 to a second potential V2 (both of these potentials are referenced to a fixed potential, such as electrical ground). In the subsequent step 102, a sensing signal Vout is provided, which is indicative of a change of a charge carried by the sensing plate 17 resulting from the change in the potential difference between the finger 11 and the sensing plate 17 resulting from the potential change in step 101.

The person skilled in the art realizes that the present invention by no means is limited to the preferred embodiments described above. On the contrary, many modifications and variations are possible within the scope of the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A capacitive fingerprint sensing device for sensing a fingerprint pattern of a finger, said fingerprint sensing device comprising a semiconductor substrate; and an array of sensing elements formed on said semiconductor substrate,
   wherein each of said sensing elements comprises:
   a protective dielectric top layer to be touched by said finger;
   an electrically conductive sensing structure arranged underneath said top layer; and
   a charge amplifier connected to said sensing structure for providing a sensing signal indicative of a change of a charge carried by said sensing structure resulting from a change in a potential difference between said finger and said sensing structure, said charge amplifier comprising:
   a negative input connected to said sensing structure;
   a positive input;
   an output providing said sensing signal;
   a feedback capacitor connected between said negative input and said output; and
   a sense transistor having a gate constituting said negative input,
   wherein said sense transistor is formed in a well in said semiconductor substrate, an interface between said well and said substrate being configured in such a way that current can be prevented from flowing between said well and said substrate; and
   wherein said charge amplifier is configured in such a way that a potential at said negative input substantially follows a potential at said positive input,
   wherein said fingerprint sensing device further comprises:
   excitation signal providing circuitry, said excitation signal providing circuitry being:
   connected to said positive input and configured to change a potential at said positive input from a first potential to a second potential, to thereby change a potential of said sensing structure, thereby providing said change in potential difference between said finger and said sensing structure; and
   connected to said well for changing a potential of said well from a third potential to a fourth potential, a difference between said third potential and said fourth potential being substantially equal to a difference between said first potential and said second potential, to thereby reduce an influence of a parasitic capacitance between said sensing structure and said well.

2. The fingerprint sensing device according to claim 1, wherein said excitation signal providing circuitry is further configured to:
   simultaneously keep said positive input of the charge amplifier at the first potential and said well at the third potential; and
   simultaneously keep said positive input of the charge amplifier at the second potential and said well at the fourth potential.

3. The fingerprint sensing device according to claim 1, further comprises sampling circuitry connected to said output of the charge amplifier, and configured to sample said sensing signal at a first sampling time when said positive input of the charge amplifier is kept at the first potential and said well is kept at the third potential and at a second sampling time when said positive input of the charge amplifier is kept at the second potential and said well is kept at the fourth potential.

4. The fingerprint sensing device according to claim 1, wherein the third potential is substantially equal to the first potential, and the fourth potential is substantially equal to the second potential.

5. The fingerprint sensing device according to claim 1, wherein said excitation signal providing circuitry comprises an output connected to each of said positive input and said well for simultaneously changing the potential at said positive input and the potential of said well from the first potential to the second potential.

6. The fingerprint sensing device according to claim 1, further comprising a shielding structure arranged between said sensing structure and said substrate,
   wherein said excitation signal providing circuitry is further connected to said shielding plate and configured to change a potential of said shielding plate from a fifth potential to a sixth potential, a difference between said fifth potential and said sixth potential being substantially equal to a difference between said first potential and said second potential.

7. The fingerprint sensing device according to claim 1, wherein said sense transistor is an NMOS-transistor or a PMOS-transistor, and said well is a p-well or an n-well, respectively.

8. The fingerprint sensing device according to claim 1, wherein at least one of a p-well and an n-well is formed in said well.

9. The fingerprint sensing device according to claim 8, wherein said well is common to a plurality of sensing elements.

10. The fingerprint sensing device according to claim 1, wherein each of said sensing elements further comprises:
   a reset switch comprising at least one reset transistor connected between said negative input and said output of the charge amplifier and controllable to discharge said feedback capacitor,
   wherein said reset transistor is formed in said well.

11. The fingerprint sensing device according to claim 1, wherein each of said sensing elements further comprises:
   drive signal providing circuitry comprising at least one drive transistor connected to said sensing structure and controllable to provide a driving signal directly to said sensing structure,
   wherein said drive transistor is formed in said well.

12. The fingerprint sensing device according to claim 1, further comprising readout circuitry connected to each of said sensing elements and configured to provide a representation of said fingerprint pattern based on said sensing signal from each of said sensing elements.

13. An electronic device comprising:
   the fingerprint sensing device according to claim 12; and
   processing circuitry configured to:
      acquire said representation of said fingerprint pattern from the fingerprint sensing device;
      authenticate a user based on said representation; and
      perform at least one user-requested process only if said user is authenticated based on said representation.

14. A method of sensing a fingerprint pattern of a finger using a fingerprint sensing device comprising a doped semiconductor substrate; and an array of sensing elements formed on said semiconductor substrate, wherein each of said sensing elements includes an electrically conductive sensing structure connected to the gate of a sense transistor formed in a well in said semiconductor substrate, said well being doped to opposite polarity with respect to said semiconductor substrate, said method comprising the steps of, for each of said sensing elements:
   changing a potential of said sensing structure from a first potential to a second potential;
   changing a potential of said well from a third potential to a fourth potential, a difference between said third potential and said fourth potential being substantially equal to a difference between said first potential and said second potential; and
   providing a sensing signal indicative of a change of a charge carried by said sensing structure resulting from a change in a potential difference between said finger and said sensing structure achieved by said change in potential of the sensing structure from the first potential to the second potential.

15. The method according to claim 14, further comprising the step of:
   changing a potential of each sensing structure in a plurality of adjacent sensing elements from a seventh potential to an eighth potential, a difference between said seventh potential and said eighth potential being substantially equal to a difference between said first potential and said second potential.

* * * * *

UNITED STATES PATENT AND TRADEMARK OFFICE
CERTIFICATE OF CORRECTION

| | |
|---|---|
| PATENT NO. | : 9,152,841 B1 |
| APPLICATION NO. | : 14/548834 |
| DATED | : October 6, 2015 |
| INVENTOR(S) | : Frank Robert Riedijk |

It is certified that error appears in the above-identified patent and that said Letters Patent is hereby corrected as shown below:

On the Title Page, Please insert

--(30)    Foreign Application Priority Data

March 24, 2014   (SE) ................................. 1450336-1--

Signed and Sealed this
Eighth Day of March, 2016

Michelle K. Lee
*Director of the United States Patent and Trademark Office*